United States Patent [19]

Lew

[11] 4,085,506
[45] Apr. 25, 1978

[54] LOCKING DEVICE FOR DENTAL PROSTHESES

[76] Inventor: Isaih Lew, 29 Bayberry Dr., Pleasantville, N.Y. 10570

[21] Appl. No.: 707,604

[22] Filed: Jul. 22, 1976

[51] Int. Cl.² .............................................. A61C 13/00
[52] U.S. Cl. ...................................................... 32/2
[58] Field of Search ................... 32/10 A, 2, 3; 24/218, 24/216, 201 LP; 403/378, 379, 324

[56] References Cited

U.S. PATENT DOCUMENTS

| 1,804,951 | 5/1931 | Reiter | 24/218 |
| 3,534,640 | 10/1970 | Macy | 403/378 V |
| 3,748,739 | 7/1973 | Thibert | 32/10 A |

*Primary Examiner*—Robert Peshock

*Attorney, Agent, or Firm*—Kenneth E. Macklin

[57] ABSTRACT

A novel medical prosthesis locking device, particularly for dental prostheses, which are to be fixed and yet easily removable for maintenance, etc. The locking device comprises a cylinder which is adapted to be embedded in the prosthesis and a plunger which is adapted to be slidably mounted in the cylinder so that when the plunger is in one position, the prosthesis may be inserted and placed in position within the mouth; and in another position the plunger engages an orifice in an immovable fixture in the mouth, e.g., abutment teeth crowned with short bar extensions containing holes properly aligned with and receptive of the locking end of the plunger of the locking device when the prosthesis is in position.

7 Claims, 8 Drawing Figures

LOCKING DEVICE FOR DENTAL PROSTHESES

BACKGROUND OF THE INVENTION

Securing of medical prostheses to parts of the body has presented many problems, to which solutions have been proposed which do not adequately resolve the problems. Dental prostheses particularly present problems because in many instances the prostheses are required to be securely fixed in position and yet easily removed for inspection, maintenance and cleaning. For example, in the management of the atrophic mandible and maxilla the retention of questionable remaining teeth and roots often requires that a series of roots and root substitutes (i.e. screws, blades, sub-periosteal implants) be tied together around the arch with gold thimble copings attached to each other with a gold bar (or a bar of other metal) for mutual support. The functioning prosthesis is incorporated in a superstructure consisting of closely adapted acrylic base which supports the teeth in function. This acrylic base fits snuggly over the bar and contiguous mucosa. Radiographic functional studies indicate that such prostheses shift three-dimensionally relative to the dental ridge underlying the prosthesis, i.e., the prostheses move anteriorly-posteriorly, superiorly-inferiorly, and laterally. Therefore, to avoid excessive torquing on the supporting roots and implants, the acrylic base is allowed to exhibit slight movement for stress dissipation. In many patients, as the acrylic wears internally, the superstructure can become so loose as to be easily dislodged during comminution of food, or unconcious movement of tongue and cheek.

DESCRIPTION OF THE PRIOR ART

Several devices have been used to provide mechanical means in addition to friction fit in order to retain the prosthesis in place positively. One is the commonly used bridge wire (clasp) around a permanent tooth. Over a period of time the torquing action produced by the wire (clasp) as the denture moves, will cause the loosening of the permanent tooth. Another device is a spring-loaded ball device in the prosthesis at the point where the prosthesis will abut a permanent tooth. The permanent tooth is capped and a socket is formed in the cap so that the ball in the prosthesis will fit into it. The disadvantage with this device is that the constant pressure of the ball on the permanent tooth tends to dislocate that tooth and loosen it. In addition it is not an adequate locking device. A third device which has been used is a lever at the buccal side of the prosthesis. The lever is pivoted to the prosthesis at one end and the other end has a hook which when pushed through a slot in the prosthesis is able to engage a root substitute underlying the base of the prosthesis. Some of the disadvantages of this device are that it is awkward to use; it is not as positive a locking device as is desired; and it does not provide for stress dissipation to overcome torque forces when the prosthesis is functioning.

SUMMARY OF THE INVENTION

It is an object of this invention to provide a locking device for medical prostheses.

More particularly, it is an object of this invention to provide a locking device for dental prostheses.

It is an object of this invention to provide a locking device for dental prostheses which positively locks the prostheses in place and yet allows for easy removal of the prostheses by the wearers.

It is a still further object of this invention to provide a locking device for dental prostheses which is adapted to dissipate stress on implants, mucosa underlying the prostheses, and permanent teeth - particularly caused by torque during functioning of the prostheses, e.g., as in comminution of food.

It is a still further object of this invention to provide a device which is safe to the wearer, readily cleanable, comfortable to the wearer, small enough so as not to offend surrounding tissue (cheek and tongue), and relatively unnoticeable to others.

It is also an object of this invention to provide a device which may be used with a variety of dental prostheses in the treatment and maintenance of a variety of situations encountered in the atrophied mandible and maxilla.

Generally, the locking device of this invention is comprised of a cylinder adapted to be affixed to or in a prosthesis, a slidably mounted plunger in the cylinder, the plunger being graspable at one end so that it may be slid back and forth in the cylinder in such a way that at one position the plunger extends from the opposite end of the cylinder thereby being engagable in a suitable orifice in a permanent fixture in the mouth, e.g., a short bar extension on a crowned abutment tooth, to which it is to be attached. At another position the plunger is retracted sufficiently so that the plunger is disengaged from the orifice. Preferably, there is a means for retaining the plunger in the locked position when desired. Also, there is preferably a means for retaining the plunger in the cylinder so that it is not readily removed or lost from the cylinder.

DESCRIPTION OF THE PREFERRED EMBODIMENTS

Figure 1A:
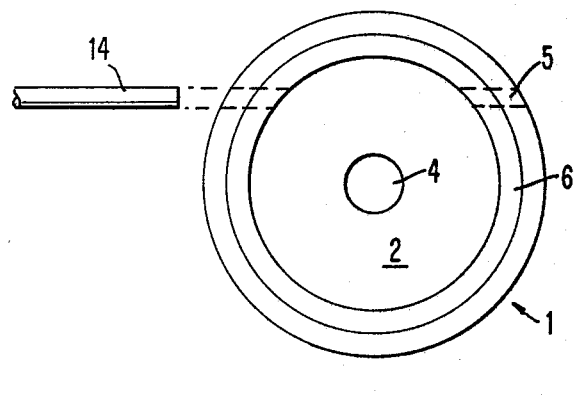
FIG. 1a is a view of the cylinder from the end into which the plunger fits.
Figure 1B:
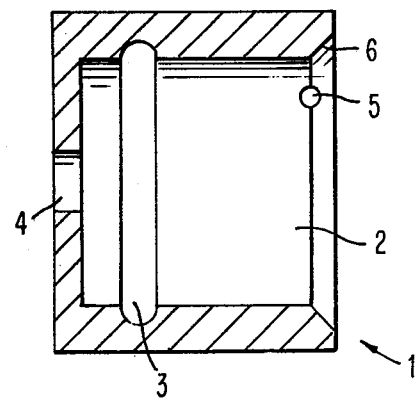
FIG. 1b is a cross-sectional side view of the cylinder.

FIGS. 1a, 1b, 2a and 2b illustrate the preferred configurations of the two basic components of the locking devices of this invention. FIGS. 1a and 1b respectively show an end view and cross-sectional side view of the cylinder component 1. The cylinder is preferably machined from a material which will not be corroded in its intended environment, e.g., the mouth. The material may be stainless steel or titanium. The cylinder contains plunger chamber 2, which in turn has ring groove 3 around its perimeter adapted to receive split spring ring 20, which is shown in FIG. 3.

Figure 2A:
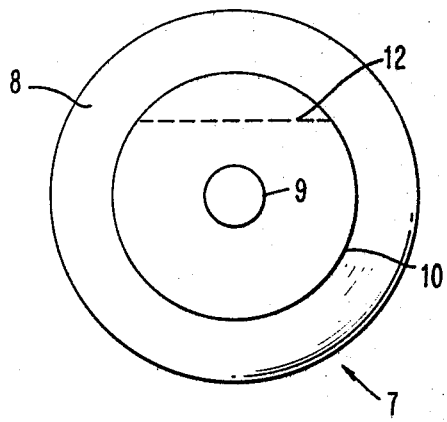
FIG. 2a is a view of the plunger from the end which fits into the cylinder.
Figure 2B:
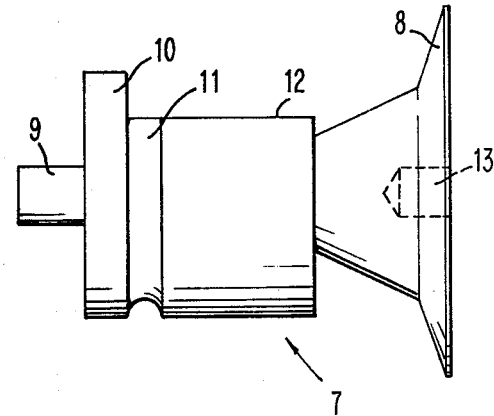
FIG. 2b is a side view of the plunger.

FIGS. 2a and 2b respectively show a locking end view and a side view of the plunger 7 which is adapted to fit into the plunger chamber 2, i.e., plunger 7 shown in FIG. 2b moved leftward into plunger chamber 2 shown in FIG. 1b. Cylinder component 1 has a chamfer 6 to ease the insertion of plunger 7 into chamber 2. Button 8 is graspable to move the plunger 7 into and out of the plunger chamber 2. When plunger 7 is inserted to the maximum in plunger chamber 2, rod portion 9 of plunger 7 partially protrudes from orifice 4 of the cylinder component 1. Similarly when button 8 is grasped and the plunger moved outward from the plunger chamber 2 the rod portion 9 no longer protrudes from orifice 4. Plunger 7 has groove 11 which is adapted to receive split spring ring 20.

Figure 3:
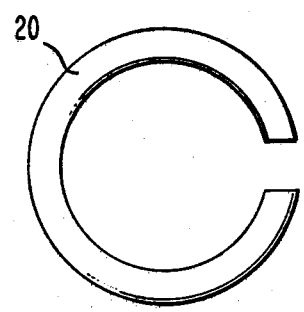
FIG. 3 is a view of the split spring ring which fits around the plunger and inside the cylinder.
Figure 5:
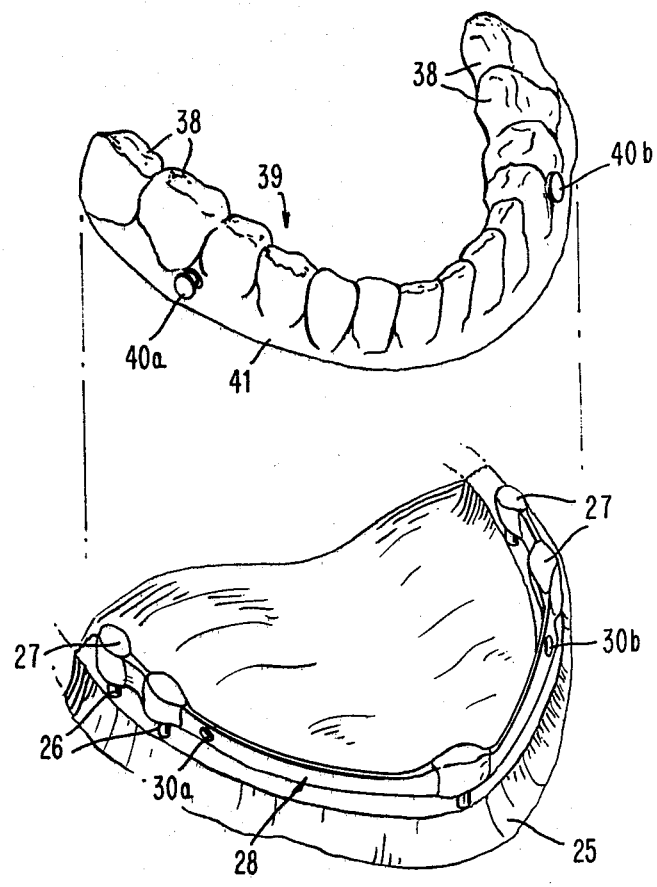
FIG. 5 shows an atrophied mandible with endosseous implants in place and copings joined with bar. Above it is shown an overlay prosthesis with superstructure containing the locking devices of this invention, one in "open" and one in "locked" position.

FIG. 3 shows split spring ring 20, which has an outside diameter which is larger than the diameter of groove 3, but not so much larger that the ring cannot be compressed to fit in groove 3. Groove 11 and flat portion 12 (if it is present in the most preferred embodiment) are so dimensioned on plunger 7 as to allow split ring 20 space to be compressed as the plunger 7 with split spring ring 20 in place is pressed into place in plunger chamber 2 in cylinder component 1. In assembling the preferred locking device of this invention, it is preferred for ease of assembly that the split spring ring 20 be placed in groove 11 of plunger 7, and then plunger 7 with split spring ring 20 in place be inserted into plunger chamber 2 of cylinder component 1. If split spring ring 20 is in place in groove 11, in a preferred embodiment, then when plunger 7 is inserted in the plunger chamber 2 to the maximum, the ring will expand and snap into groove 3 of plunger chamber 2, thereby retaining the plunger in locked position and rod portion 9 protruding so that it may engage a suitable orifice in a fixture in the mouth, e.g., holes 30a and 30b in a bar 28 attached to copings 27 on endosseous implants 26 in atrophied mandible 25, as illustrated in FIG. 5. When button 8 is grasped and pulled, plunger 7 may be totally removed from plunger chamber 2.

Figure 4A:
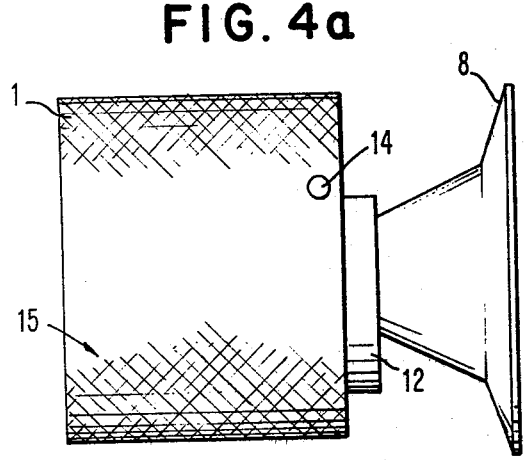
FIG. 4a shows the assembled device with the plunger in the "open" position.
Figure 4B:
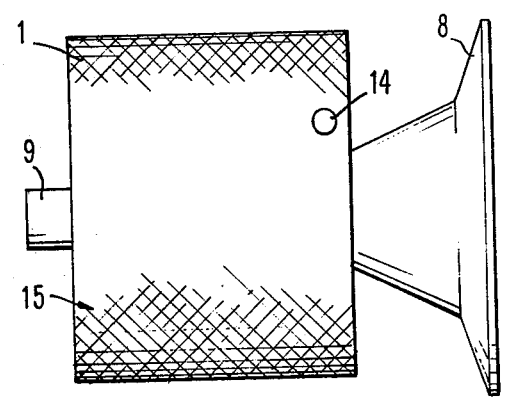
FIG. 4b shows the assembled device with the plunger in the "locked" position.

To retain plunger 7 in the chamber 2 of the assembled device shown in FIGS. 4a and 4b, it is preferred to insert pin 14 shown in FIG. 1 into hole 5 in cylinder component 1 and through plunger chamber 2 when preferred flat portion 12 on plunger 7 is aligned with the side of the hole 5 close to the center of the cylinder component 1. The ends of pin 14 may then be peened or bent to prevent the pin from falling out of hole 5. With the pin in place in the assembled device, the plunger 7 is prevented from being removed from the cylinder component 1 because portion 10 of plunger 7 cannot pass pin 14. Button 8 is shown with a cylindrical depression 13, which is useful as an anchoring area for a gum-colored acrylic coating on the button when the locking device is incorporated in the "gum" portion 41 of a dental prosthesis 39 illustrated in FIG. 5.

FIG. 4a shows the locking device in the "open" position. FIG. 4b shows the device in the "closed" or "locking" position. FIG. 5 shows 40a and 40b, which are locking devices of this invention embedded in the buccal sides of the "gum" portion 41 of a dental prosthesis 39 containing "teeth" 38. The locking device 40a is shown in the "open" position. The locking device 40b of this invention is shown in the "closed" or "locked" position, in which rod 9 would engage the hole 30b in the bar 28 depicted in FIG. 5 if the prosthesis were in place on the frame below it, where the bar 28 is attached to copings 27 on implants 26 in atrophied mandible 25.

The locking device of this invention may be secured to the acrylic superstructure of a dental prosthesis in the following way: First a carbide drill of the same diameter as rod portion 9 is used to cut a hole to receive the rod portion 9 in, e.g., the gold bar framework which is permanently cemented to roots or implant heads. The drilled hole in the gold bar is marked with a dye marker and the superstructure is seated on the framework, thereby transferring marker to the undersurface of the superstructure base and marking where the locking device is to be positioned. Using a large round acrylic burr, a hole in the acrylic base is made larger than the outer diameter of the cylinder component 1. With the acrylic superstructure over the gold bar the locking device of this invention, in locked position, is fitted into the hole in the superstructure so that the rod portion 9 fits into the hole in the gold bar, e.g., holes 30a and 30b. The locking device is fitted into the prepared hole in the superstructure with self-polymerizing methyl methacrylate. Preferably the outside surface of the cylinder component 1 is knurled 15, as shown in FIGS. 4a and 4b, or otherwise roughened to provide mechanical "tooth" and therefore better bonding to the prosthesis. The button 8 protruding buccally from the denture base may be painted with base color acrylic which is allowed to set and then polished flush to the existing superstructure, leaving a slight undercut anteriorly and posteriorly for easy manipulation of the button by the patient's finger nails.

When the superstructure of the dental prosthesis is placed in position over the gold bar framework in the patient's mouth, the patient closes teeth in occlusion and presses slightly on button(s) 8, thereby locking the prosthesis in position. The patient may remove the prosthesis just as easily by pulling out the button(s) 8 by a slight nail or finger pull on it (them).

In the most preferred embodiment containing the split spring ring 20 and the retaining pin 14, there are two positions which will hold - (a) the locked position where rod portion 9 enters a hole in the gold bar and the spring ring 20 snaps into the groove 3 of the chamber 2, and (b) the open position where the button is pulled away from the bar and the rod portion 9 is therefore flush with the undersurface of the superstructure of the prosthesis, thereby freeing the prosthesis for removal and easy cleansing or adjustment. For example, mobility can be introduced by making holes in the bar oversized to allow for lessened stress on supporting roots or implants.

In partial prosthesis, the locking device can be used by crowning the abutment teeth with short bar extensions in which holes can be drilled. Then the locking device can be inserted in buccal extension of the acrylic superstructure of the partial prosthesis.

Where only unilateral attachment of the prosthesis is possible, it is desirable to make the hole in the bar oversized in order to allow the dissipation of torque in the unsupported end of the prosthesis, which is displaceable in compressive function.

The locking device of this invention may be made in any convenient size relative to the prosthesis into which it will be fitted. Its design is such that it can be made quite small in size and yet effective. Suitable overall dimensions for a dental prosthesic locking device are about 5/32 inches for the outside diameter of the cylinder component 1 shown in FIGS. 1a and 1b, slightly over ¼ inches for the length of plunger 7 shown in FIG. 2b, and about 3/16 inches for the diameter of button 8 of plunger 7.

Variations and modifications may be made in the foregoing specification and in the claims without departing from the scope and spirit of the invention, and portions of the improvements of the invention may be used without others.

I claim:

1. A locking device (especially useful) for dental prostheses, which comprises:
   (a) a hollow cylinder with openings at both ends, which is adapted to be affixed to or in a dental prosthesis, and
   (b) a plunger slidably mounted in the cylinder so that the locking end of the plunger may be extended from one end of the cylinder or substantially retracted to that end of the cylinder as the plunger is slid into or away from the cylinder by the manipulation of the other end of the plunger; whereby when extended from the cylinder affixed to or in a dental prosthesis in the mouth, the end of the plunger engages an orifice in a fixture in the mouth and when retracted into the cylinder, the end of the plunger is withdrawn from the orifice in the fixture in the mouth, thereby respectively locking the the prosthesis to the fixture or unlocking it from the fixture.

2. A locking device as claimed in claim 1, which comprises:
   (a) a hollow cylinder with openings at both ends, which is adapted to be affixed to or in a dental prosthesis,
   (b) a plunger slidably mounted in the cylinder and so adapted that the locking end of the plunger may be extended from one end of the cylinder or substantially retracted to that end of the cylinder as the plunger is slid into or away from the cylinder by manipulation of the other end of the plunger, and
   (c) a retaining means adapted to retain the locking end of the plunger in the extended position when the opposite end of the plunger is manipulated so as to slide the plunger into the cylinder component.

3. A locking device as claimed in claim 1, which comprises:
   (a) a hollow cylinder with openings at both ends, which is adapted to be affixed to or in a dental prosthesis,
   (b) a plunger slidably mounted in the cylinder and so adapted that the locking end of the plunger may be extended from one end of the cylinder or substantially retracted to that end of the cylinder as the plunger is slid into or away from the cylinder by manipulation of the other end of the plunger.
   (c) a retaining means adapted to retain the locking end of the plunger in the extended position when the opposite end of the plunger is manipulated so as to slide the plunger into the cylinder components, and
   (d) a second retaining means adapted to retain the plunger and keep it from being removed from the cylinder component.

4. A locking device as claimed in claim 1, in which the hollow cylinder (a) has an opening at one end which is smaller than the opening at the other end and the plunger has a portion which is correspondingly smaller so that it may pass through the smaller opening of the hollow cylinder.

5. A locking device as claimed in claim 2, in which the hollow cylinder (a) has a groove around its inner perimeter; retaining means (c) is a split spring ring of such a thickness and outside diameter that it fits within the groove in hollow cylinder (a); plunger (b) contains a groove of a thickness and diameter that will accommodate the inside diameter of the split spring ring; and the grooves in the hollow cylinder (a) and on plunger (b) are of such relative diameters that the split spring ring has sufficient room to expand and contract as the plunger is slid to and fro in the hollow cylinder, and the grooves are so positioned in the hollow cylinder and on the plunger that when the plunger is in the hollow cylinder in such a position that the split spring ring is in both grooves, the locking end of the plunger extends from the hollow cylinder.

6. A locking device as claimed in claim 1 in which there is a hole through the wall of the hollow cylinder (a) intersecting the hollow and off-center of the center of the cylinder; there is a flat portion on the side of the plunger (b) and parallel to its axis and away from the locking end of the plunger; and there is a retaining pin placed through the hole in the wall of the hollow cylinder after the plunger is in place with its flat portion aligned with the bottom line of the hole through the wall of the cylinder.

7. A locking device as claimed in claim 1 in which the outside surface of the hollow cylinder (a) is knurled.

* * * * *